(12) United States Patent
Carothers et al.

(10) Patent No.: US 8,974,848 B1
(45) Date of Patent: Mar. 10, 2015

(54) INGESTIBLE PRODUCT AND METHOD FOR ENHANCING THE APPEARANCE AND QUALITY OF TEETH IN-VIVO

(76) Inventors: Barry W. Carothers, Dallas, TX (US); Donald N. Riggs, Fort Worth, TX (US)

( * ) Notice: Subject to any disclaimer, the term of this patent is extended or adjusted under 35 U.S.C. 154(b) by 849 days.

(21) Appl. No.: 12/380,264

(22) Filed: Feb. 26, 2009

Related U.S. Application Data

(60) Provisional application No. 61/133,084, filed on Jun. 26, 2008.

(51) Int. Cl.
*A61C 15/00* (2006.01)

(52) U.S. Cl.
USPC .......... 426/590; 426/594; 426/597; 424/1.73; 424/729

(58) Field of Classification Search
USPC ........................................ 514/560
See application file for complete search history.

(56) References Cited

U.S. PATENT DOCUMENTS

| | | | | |
|---|---|---|---|---|
| 3,108,877 | A | * 10/1963 | Cooper | 426/52 |
| 6,180,159 | B1 | * 1/2001 | Villagran et al. | 426/590 |
| 2006/0018843 | A1 | 1/2006 | Fine | |
| 2006/0020031 | A1 | * 1/2006 | Berlin | 514/560 |
| 2008/0247973 | A1 | 10/2008 | Baig et al. | |

FOREIGN PATENT DOCUMENTS

| | | | | |
|---|---|---|---|---|
| GB | 2378693 | * | 2/2003 | A61K 9/48 |
| WO | PCT/US 2010/000558 | | 4/2010 | |

* cited by examiner

*Primary Examiner* — Walter Webb

(57) ABSTRACT

Tooth stain resulting from exposure to coloring agents contained in food and beverages, generally termed foodstuffs, is reduced, prevented and/or reversed by the addition of consumable anti-staining materials to the foodstuff anytime prior to ingestion. The anti-staining materials may be introduced into the foodstuff during the manufacturing process or added by the consumer at the time of preparation or use. A number of materials which interact with tooth stains and/or staining agents to counteract their effect and/or reduce their coloration as well as substances which interact with teeth to block the interaction of staining agents with teeth are disclosed.

11 Claims, 2 Drawing Sheets

Fig. 4
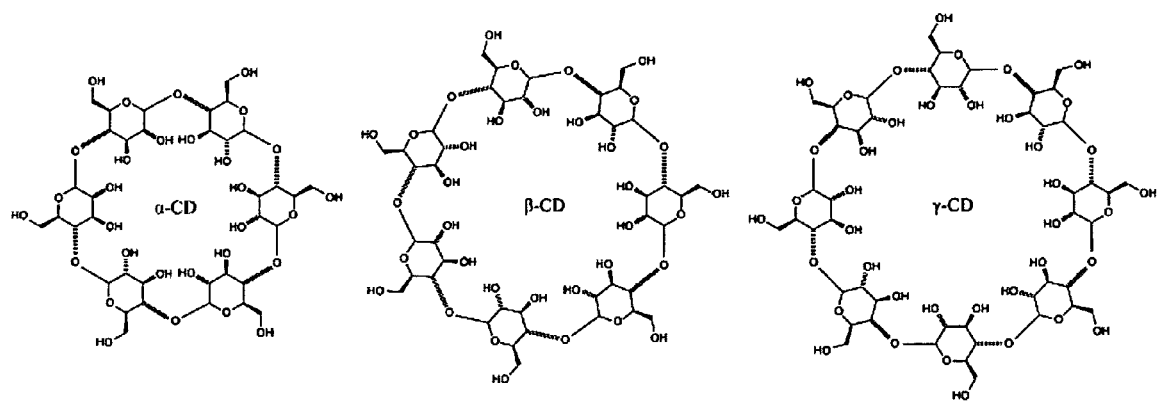
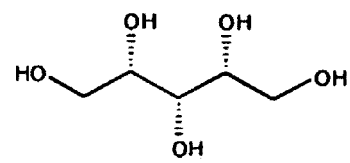
Fig. 5

INGESTIBLE PRODUCT AND METHOD FOR ENHANCING THE APPEARANCE AND QUALITY OF TEETH IN-VIVO

CROSS-REFERENCE TO RELATED APPLICATIONS

This application was first filed as U.S. Provisional Patent Application Ser. No. 61/133,084 filed Jun. 26, 2008.

BACKGROUND OF THE INVENTION

1. Field of the Invention

The invention resides in the field of the care and maintenance of teeth; and more particularly relates to products which are added to foodstuffs and to methods which prevent and reduce the staining of teeth in-vivo.

2. Description of the Prior Art

A. Tooth Staining

Tooth staining is a well known concern of the present day consumer; and this problem has been addressed by a myriad of products commonly available in today's commercial markets. The conventionally available items include whitening strips, dentifrices, toothpastes, chewing gum, and the like. Furthermore, professional treatments at dental clinics are also commonly available.

There are also various methods used today for limiting tooth staining, or for whitening the teeth once they are stained. One such method is for the person to brush his teeth immediately after eating staining foods or to use a straw for drinking colored liquids. However, even with vigorous tooth brushing, the buildup of stains caused by the ingestion of food and drink will take place gradually over time.

As an alternative, others methods employ whitening compositions to remove stains after they have darkened the teeth. Those whitening compositions currently on the market typically use manual application delivery methods such as chewing gum or dental trays to apply the whiteners to the surface of the stained teeth.

It will be recognized and appreciated also that the commercial products and conventional procedures currently in use are intended to remove existing stains which are already present as a result of staining agents in food and beverages reacting with teeth. These typically include food and beverage colorants commonly to be found in such beverages as coffee, tea, wine, vegetable and fruit juices, colas and soft drinks; and in such foods as beets, pomegranates, filled pastries, and sauces. Tobacco and bacteria are also major contributors to tooth stains.

Nevertheless, in so far as is presently known, no tooth whitening product or method exists today which has utilized the concept of or has provided a harmless or beneficial, non-toxic, and biocompatible ingestible material or mixture of ingredients which is to be added to and mixed with a consumable substance, particularly at any time prior to the moment of ingestion; and which will prevent or markedly reduce the staining effects of whatever staining or colored agents are then present within the solid food or liquid beverage on human teeth after ingestion.

B. Textile Stain-Neutralizing Agents

Although unrelated in any sense to tooth whitening compositions, some stain removing agents have been developed for use with textiles, fabrics, carpets, and the like. Among these, a few products are directed to neutralizing the effects of staining agents contained in FDA-approved food coloring agents when such color dyed foods are inadvertently spilled onto carpets, textiles, or other fabric materials. Attention is directed to: U.S. Pat. No. 5,096,726 of Keown et al.; U.S. Pat. No. 5,571,551 of Fusi et al.; and U.S. Pat. No. 5,681,604 of Li et al., as describing several representative and illustrative examples of conventionally known stain-neutralizing agents. However, none of these conventionally known stain-neutralizing agents are suitable for in-vivo usage, particularly the human mouth; none of these compositions are concerned with reducing the staining of human teeth; and none of these constitute a non-toxic and biocompatible prepared product which can be introduced by a consumer into his food or beverage at any time prior to ingestion.

In addition, the focus of these textile oriented prior art patents is centered upon the use of gallotannins and similarly related compounds, such as the extracts of a gall nut or similar nut-bearing plant. These gallotannins and similarly related compounds prevent the occurrence of a specific chemical interaction with members constituting the class of FDA-approved food-dyes; with specific TO textiles such as primarily synthetics (including polyesters and nylon); and with natural fibers such as cotton, linen and wool. It will be noted and appreciated also that since of the structural and chemical makeup of oral surfaces in-vivo (such as human teeth dentine and the oral mucosa of the mouth) bear little resemblance to any textile or fabric article of manufacture, the current invention differs and is easily distinguished from these textile oriented products in all relevant details.

C. Current Status

Accordingly, in so far as is known to date, there has been no development of any product nor generation of any process having stain abating properties and capabilities which is suitable and biocompatible with either ingestible foodstuffs or the surfaces of live teeth. Equally important, there has been no awareness or consideration of any means or manner for lightening or reducing the staining of human teeth in-vivo by incorporating a prepared product into a foodstuff prior to its ingestion. In this regard, it is recognized that tooth lightening via the surface application of a particular peroxide additive and/or an addition of enzymes is a commonly known and conventionally employed practice but it must be appreciated also that these tooth whitening compounds and these techniques can not be used with and are not intended for an ingestible and consumable food or beverage.

SUMMARY OF THE INVENTION

The present invention is a prepared in-advance product and a method for preventing and/or reducing tooth staining by the use of substances and compounds which individually, as well as in combination, interact with staining agents then existing and occurring in solid foods and beverages (collectively known as "ingestible foodstuffs"), and will subsequently interact with teeth in-vivo, to block or reverse the adhesion of such staining agents to tooth surfaces. All of the materials disclosed herein for this purpose are orally ingestible, consumable, and can be mixed directly with the solid or liquid foodstuff either at the time of food manufacture, or food preparation, or immediately prior to swallowing.

Additionally, these substances and compositions are all water soluble, water miscible, or water suspendable; and can be prepared and supplied in a solid, powder, or liquid format that may advantageously be added to and mixed with a foodstuff by a consumer at will anytime prior to actual ingestion.

The different kinds and types of materials which are suitable for use with the current invention include: the class of materials that oxidize and/or hydrolyze staining agents found in consumable foods and beverages; the class of materials that bind preemptively to oral surfaces in the human mouth and make the oral surfaces unavailable to react with the staining agents of ingestible foodstuffs; and the class of materials that bind preemptively to staining agents of ingestible foodstuffs and make such agents unavailable for binding to oral surfaces.

Some of the materials which have been found suitable for use in the present invention (and whose operation and effect will be further discussed in detail hereinafter) include but are not limited to: chitosan, PEG, starch carbohydrate, MSM, cardamon oil or extract, calcium ascorbate, waxes and other high-molecular-weight alcohols, xylitol, carbohydrates, including polyol sweeteners, starch, maltodextrin, as well as other corn syrup fractions and derivatives, and cyclodextrin. All of the above are exemplary and representative substances which are known to be biocompatible, non-toxic, and thus safe for human ingestion.

The features, capabilities, and advantages, as well as the details of the invention, will be more fully understood from the description of the preferred embodiments which follow.

DESCRIPTION OF THE DRAWINGS

FIG. 4 is the chemical formulation for Cyclodextrins;
and
FIG. 5 is the chemical formulation for Xylitol

DESCRIPTION OF THE PREFERRED EMBODIMENTS

Figure 1:
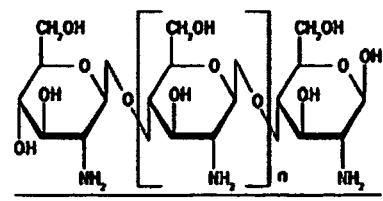
FIG. 1 is the chemical formulation for Chitosan.

To avoid ambiguity and potential misunderstandings related to nomenclature and terminology, it will be expressly understood and appreciated that the terms "foodstuff" and "foodstuffs" are each collective name and titles which intrinsically include all of the following: any ingestible liquid, beverage, or fluid fit for human consumption; any solid food, food product, or solid consumable nourishment; any pulverized or specifically processed dietary item; and any mixture or blending of edible liquids and solids in any ratio.

The present invention presents a diverse range of prepared in advance formulated products that are able to inhibit and/or to minimize the discoloration of human teeth in-vivo which is caused by staining agents intrinsically present in foodstuffs, the foods and beverages people consume each day for sustenance. These prepared formulated products act to reduce the amount and/or the coloring capability of staining agents in consumable foodstuffs in multiple ways often by ligating such staining agents as are then present to another molecule or entity and then effectively keeping the staining agents sequestered; or by changing the food or drink color, properties or pigmentation; or alternatively, by reacting with the surface of the teeth to fill in the tooth pores with non-colored molecules.

The method of the present invention comprises supplying the prepared product in a solid, powered, or liquid form which may be added to the foodstuff anytime prior to ingestion, and particularly just prior to the time of consumption by the person. As the prepared product may be constituted in a diverse range of formulations and in various combinations of suitable ingredients which are collectively capable of reacting with a variety of the known causes of tooth staining, it is particularly advantageous to be able to add the preparation at the time of consumption, and at the option and convenience of the individual consumer.

Unforeseen Advantages and Unexpected Benefits

Accordingly, depending upon the specific formulated mixture of ingredients as selected from the range of representative substances set forth below, a number of unexpected features, major advantages, and highly desirable attributes will be provided by and be characteristic of the invention. For example, the various formulations of the present invention will routinely help prevent food and beverages from staining teeth; will progressively continue to whiten teeth in-vivo; will provide a biocompatible protective barrier between teeth and staining colorants; will enhance capillary blood circulation in the gums; and will prevent bacteria and other microorganisms from adhering to teeth and oral tissue (mucus membranes) in the human mouth.

Also, when used in isolation, the prepared product may be used and is effective as a powdered dentifrice. In this format, the prepared product will precipitate staining materials from consumable food and beverages; will be anti-bacterial in the normally acidic oral environment and help prevent bacteria growth and retention in the mouth and gastro-intestinal environment; will neutralize stains within tooth enamel; will denature stains within tooth enamel; will retard the formation of dental plaque and calculus; will prevent cavities; will break many of the bonds that attach calculus to tooth enamel; and will deposit a healthy residue containing one or more of the product's materials on tooth enamel and other surfaces, which residue will interfere with deposition of further stains.

In general, therefore, the capabilities of the formulated dental product can provide the following actions:
Help prevent liquids and foods such from staining teeth;
Whiten teeth;
Remineralize teeth;
Provide a barrier between teeth and colorants;
Enhance capillary blood circulation in the gums;
Prevent bacteria from adhering to teeth and oral tissue;
Precipitate staining materials from liquids and foods;
Act as an anti-bacterial to prevent bacteria growth and retention in the mouth;
Retard the formation of dental plaque and calculus;
Prevent cavities; and
Break the bonds that attach calculus to tooth enamel.

I. The Underlying Problem: Tooth Staining

Tooth staining is a consequence of the effect that particular chemical substances have on the composition and structure of human teeth in-vivo; and is the proteinaceous pellicle formed on teeth and oral surfaces by staining agents, including but not limited to saliva. A human tooth is made up of an inner dentin layer and an outer enamel layer. The outer enamel layer is the protective layer of the tooth; and the enamel layer is typically opaque white or slightly off-white in its pristine form.

As has long been recognized, the enamel layer and/or pellicle can become discolored over time. Staining of the teeth in-vivo occurs primarily by the chemical binding of staining agents with the pellicle and/or the calcium phosphate or proteins found within the matrix of teeth, and by entrapment of staining agents within the numerous small pores found on the surface of living teeth.

Over the course of time and normal living conditions, heavily pigmented foods such as soy sauce, berries, and cherries will stain teeth. Also, colored drinks such as coffee, colas, wine and other dark-colored soft drinks, teas, and fruit juices such as cranberry juice can and will cause tooth staining. As related above, coffee, tea, cola, and red wine are all well-known chromogenic agents.

Similarly, chromogenic foods are also known to cause tooth discoloration. The term "chromogenic foods" simply refers to foodstuffs, which includes foods and beverages, that when consumed over time, have the ability to produce a staining effect on living teeth.

The Chemistry of Living Teeth

Tooth enamel is almost entirely composed of hydroxyapatite, a form of calcium phosphate ($Ca_5(PO_4)_3OH$). The chemical process of the formation of enamel on erupted teeth is called mineralization. It is a combination of calcium, phosphate, and hydroxyl ions in saliva resulting in calcium phosphate crystal formation on the tooth surface. Tannins and other Polyphenols are among the main ingredients in beverages and food that cause tooth discoloration. The product of the invention will reverse and/or prevent/inhibit tannins and many of the other food ingredients from staining tooth enamel.

Among the various known mechanisms by which food/liquid based staining of teeth occurs, and against which the present invention protects, are the following:

(1) Chemical bonding—frequently hydrogen bonding;

(2) Electrostatic adhesion—where a charge-differential exists between at least one end of the colorant molecule and the tooth surface;

(3) Mechanical entrainment in the pores—where a colorant molecule enters a pore or defect area in the tooth surface which pore/defect is a good mechanical fit for the molecule; and (4) Impurities in the salivary mineralization process (mechanical entrapment of organic debris and impurities in the tooth's pores and crystalline structure as it grows over time)

Any given stain caused by an ingestible foodstuff on a living tooth is usually one or a combination of the above identified mechanisms of action.

II. The Prepared Dental Product and the Manner of its Activity

The prepared product for preventing tooth staining is a dental formulation comprised of one or more of the following eight (8) essential substances: natural or synthetic waxes; proteins and/or enzymes; protein-splitting enzymes; starches and other complex carbohydrates; glycols and polyglycols; herbal oils and extracts; substituted and derivatized sulfones; monosaccharides, polysaccharides, or oligosaccharides; and cellulose-like biopolymers. The chosen in-advance single ingredient or blended mixture of ingredients can be prepared in alternative physical formats—i.e., as a powder, liquid, capsule, or tablet which can be added into or otherwise combined with the drink or edibles to be orally ingested and consumed as nourishment by the person. One or more of the listed classes of suitable essential ingredients—when suspended, distributed, or dissolved in the drink or food—will dissolve, soften, oxidize, or hydrolyze oral stain materials; and/or encapsulate or surround the teeth, by one or more of the above-listed mechanisms; and will keep colorants (i.e. staining agents) from making contact or adhering to either the pellicle or calcium phosphate (tooth enamel) or to other exposed tooth and oral materials, such as pellicle, dentin, bone, or synthetic restorative materials.

The Different Formulations and Alternative Modes of Activity

There are several categories of formulation and alternative different modes of action/activity by which the prepared in-advance dental composition can operate to reduce or reverse the staining potential of foods and beverages, thereby keeping teeth from staining.

1. A first category and mode of action is a formulated dental preparation which preemptively occupies the same binding sites or reacts with the same moieties on the teeth as do the colorants or staining agents—thereby making such dental biding sites and reactive moieties chemically unavailable to the colorants or staining agents for binding. In one preferred embodiment of this type, this formulated dental product comprises one or more members of the chemical category including but not limited to chitosan; PEG; starches; and proteins. These compositions will interfere with the staining capability of certain colorant materials in food and/or beverages which are represented by tannins, terpenes, catechols, polyphenols, and food colorings.

2. A second category and mode of action is a formulated substance which envelopes, encompasses, or surrounds the colorant/staining agent(s) then present in the foodstuff—thereby forming a protective barrier that keeps the colorant or staining agent separate, apart, and removed from oral surfaces in-vivo. In a preferred embodiment of this second type, the formulated dental product is one or more members of the category including but not limited to: glycols such as polyethylene glycol; starches; cyclodextrins; and carbohydrates such as polyol sweeteners, starch, maltodextrin, and other corn syrup fractions and derivatives, and similarly related carbohydrates.

3. A third category and mode of activity is a prepared dental product which acts to prevent the staining of teeth by oiling or waxing the surface of teeth to prevent stain penetration or adhesion. In a preferred embodiment of this third type, the dental formulation includes, but is not limited to waxes and other high-molecular-weight monohydric alcohols which are either naturally occurring or are chemically synthesized. One example is carnauba wax—which can be delivered in the beverage as an emulsion or solution; will adhere to and infiltrate the tooth surface to prevent coloration caused by the adhesion of staining materials in foodstuffs; and by physical means such as filling surface imperfections, will provide a chemically unfriendly surface for binding reactions, and contribute both gloss and luster to the teeth.

4. A fourth category and mode of activity is a prepared product which acts to denature stains or the pellicle-proteins involved in stain retention by either oxidative or enzyme-hydrolytic chemical reaction. In a preferred embodiment representative of this fourth type, the prepared in-advance dental formulation includes but is not limited to: Food Grade Hydrogen Peroxide; and those orally acceptable enzymes (including but not limited to proteases) which work by hydrolyzing and/or oxidizing coloring or staining agents, thereby rendering the resultant reaction-products colorless and more easily disrupted.

5. Other categories of prepared formulations and alternative modes of activity are also intended by the present invention. Some of these additional offerings provide a prepared dental formulation which inhibits staining by killing bacteria and preventing bacterial adhesion to teeth. Other embodiments will function to dissolve stains and keep them in solution for passage through the oral cavity environment. In these alternative instances, an exemplary embodiment is one or more materials including, but not limited to PEG, enzymes, and proteases.

III. The Formulated Dental Product

The present invention offers and provides a wide range and variety of different dental formulations comprised of essential and non-essential (i.e., discretionary and optionally present) ingredients. As used herein, the term "essential" is understood to mean that the substance or ingredient must be present in some physical form and in a measurable degree as a chemical compound in each and every embodiment of the formulated dental product. This requirement and demand is met by the existence and presence of at least one such essential substance in the formulation; but the appearance of two or more different kinds of essential substances in a single formulation will often occur, and is preferable in many instances of usage.

The expected range and variety of formulated embodiments will typically also utilize one or more non-essential or optionally added compounds and compositions. These optionally present ingredients are voluntary choice additions to the minimal dental formulations; and as non-requisite and freely elective choice additions to the minimal dental formulations, will provide properties and enhancements which are frequently very desirable for making a commercially salable product as a whole. It is explicitly recognized and understood, however, that these non-essential compounds and compositions are, individually and collectively, always optionally present; are purely non-mandatory and noncompulsory at all times; and may be freely chosen and used at will whenever it is deemed suitable to add them to the essential ingredient(s).

IV. The Choices of Essential Ingredients for the Formulated Dental Product

The following eight (8) distinct chemical classes of substances are considered essential to the present invention. Each identified category among the total of eight different essential classes can be used individually alone, or collectively in any admixture or combination with any other composition, as the requisite active ingredient(s) in the prepared in-advance dental product; and each identified substance can be placed into a liquid or solid food at any time prior to ingestion to keep teeth from staining or to reduce tooth staining in-vivo. All of the listed essential compounds are non-toxic, biocompatible, orally acceptable, and consumable after ingestion via the gastro-intestinal tract.

Chemical Class 1, Cellulose-Like Biopolymers:

The chemical class of cellulose-like biopolymers includes oligosaccharides; and is exemplified and represented by Chitosan, chitooligosaccharide, chitin, glucosamine, and other similar complex sugars. Typifying this class of substances, the stereo-chemical structure and formulation of Chitosan is shown by FIG. 1. As is readily recognized, Chitosan is a cellulose-like biopolymer complex comprised of 6-carbon monosaccharides, whose overall size and molecular weight can vary greatly.

When employed as a chosen ingredient in a prepared in advance dental formulation, Chitosan has the property of reacting with some suspended and dissolved tannins to precipitate them out of wine—a process called clarification, which is reversible in most cases by exposure to a low-pH environment, such as the human stomach. Chitosan therefore will help to prevent tooth staining by taking certain tannins out of solution so they can't stain teeth, and then re-release the tannins in the stomach so their health benefit is retained. Chitosan also reacts with various organic acids to form water-soluble salts, including chitosan ascorbate, chitosan acetate, chitosan nicotinate, and with the various organic acids in liquids such as coffee, stabilizing the acids and preventing flavor-degrading oxidation.

Figure 2:
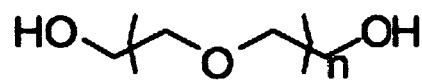
FIG. 2 is the chemical formulation for Polyethylene glycol.

Chemical Class 2, Glycols and Polyglycols:

The chemical class of glycols and polyglycols as a whole is exemplified and illustrated by Polyethylene glycol (hereinafter "PEG"), as represented structurally by FIG. 2.

PEG is well documented in the published literature as being able to inactivate tannins and make them dietarily unavailable; and much of this effect appears to be reversible at low pH, similar to Chitosan, above. Tannin unavailability is the key contribution of PEG to the reduced-staining potential for beverages provided by the prepared product. It is noted also that PEG is commonly used in animal feeds to inactivate tannins and allow more efficient protein digestion Chemical Class 3, Starch and Other Forms of Complex Carbohydrates:

By conventional definition, starch is a polyose found in all assimilating (green) plants. Typically, it is a white hygroscopic powder that can be hydrolysed to dextrin, and subsequently to d-glucose. Alternatively, enzymatic digestion of starch with the enzyme Diatase will yield maltose.

There is an interaction between starch and tannin. Starch has the ability to form hydrophobic cavities that allow inclusion complexes with tannins and many other lipophyllic molecules. Only starch, among the molecules that are bound by tannins, has this embedding characteristic.

Maltodextrin and Cyclodextrin

Figure 3:
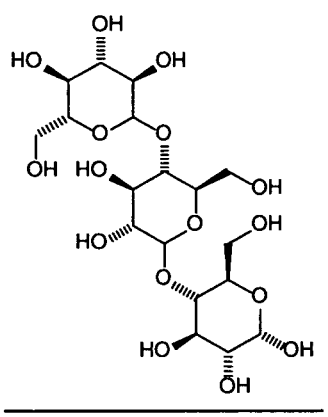
FIG. 3 is the chemical formulation for Dextran.

As noted above, Dextrins are carbohydrates formed by the hydrolysis of starch. Maltodextrin and similar dextrins such as cyclodextrin are able to bind to phosphates. In the context of the teeth, this phosphate binding would result in the formation of a thin veneer of starch on the surface of the teeth, block staining agents from access to the tooth, inhibiting discoloration. Representing this group, the structural formula of Dextran is shown by FIG. 3.

Alpha-, beta-, and gamma-cyclodextrins support the prevention of tooth-staining by a variety of mechanisms including but not limited to nutritive means, as well as chemically by occupying the same binding sites/atoms on the tooth surface which would hold the colorants. The stereo-chemical structure of these cyclodextrins is illustrated below. For descriptive purposes, the chemical structures of alpha-, beta-, and gamma-cyclodextrins are shown by FIG. 4.

Chemical Class 4, Simple and Complex Monosaccharide Alcohols:

The chemical class of simple and complex alcohols will encompass and include those compositions and chemical structures which are substitutions or derivatives of a five or six carbon sugar (i.e., a monosaccharide) that contains at least one R—OH group within its core stereo-chemical structure.

As part of this chemical class, the five and six carbon sugars containing multiple R—OH groups may occur in any of their pyranose or furanose cyclic structures; in either their aldono-lactone or aldarolactone forms; or as open-chain aldose/ketose, aldonic or aldaric substituted and/or derivatized formulations. The chemical synthesis of all such five and six carbon monosaccharides is deemed to be ordinary knowledge available to the ordinarily skilled organic synthesis chemist.

For the sake of descriptive completeness, the five and six carbon sugars will typically include: The pentose monosaccharides such as ribose, ribulose, arabinose, xylose, xylulose, and lyxose; and the hexose monosaccharides such as allose, psicose, altrose, glucose, fructose, mannose, gulose, sorbose, iodose, galactose, tagatose, and talose.

One illustrative example and representative embodiment of this category is Xylitol. As structurally presented by FIG. 5, Xylitol is a naturally-occurring, five-carbon sugar alcohol used as a sugar substitute, which has been shown to prevent tooth decay through remineriliztion of tooth enamel. It has also been shown to prevent bacterial growth, and reduce plaque and tartar build-up.

Chemical Class 5, Waxes:

As a chemical class, waxes are amorphous masses, typically composed of esters of monohydric alcohols of the higher homologues.

One preferred example is carnauba wax, which can be delivered in the beverage as an emulsion or solution; which will adhere to and infiltrate the tooth surface to prevent staining by adhesion of staining agents; and fill the surface imperfections of teeth, thereby providing a chemically unfriendly surface for binding reactions.

Chemical Class 6, Spice Oils and/or Extracts:

As a class of materials, the spice oils will include but are not limited to Cinnamon oil, Clove oil, and Cardamon oil. These oils exhibit characteristics of value to the formulated dental product. As an individual example of this class, Cardamom oil originates from the dried ripe seeds of *Electtaria caramomum*; and appears in different forms. The essential oil contains eucalyptol (cineol), sabiene, d, a-terpineol and acetate, borneol, limonene, terpene, 1-terpene-4-ol and its formate and acetate. The fixed oil consists of the glycerides of oleic, stearic, linoleic, palmitic, caprylic and caproic acids. Cardamom oil, as a representative of the class, helps prevent tooth-staining by a variety of mechanisms including killing and preventing the adhesion of bacteria on teeth, denaturing stain colorants, oiling the surface of the teeth to prevent stain penetration or adhesion.

Chemical Class 7, Enzymes Including Protein-Splitting Enzymes:

This chemical class of enzymes includes any conventionally known protein-splitting enzyme. Typically, the membership of this class is exemplified and represented by Pepsin, Trypsin, Chymotrypsin, Erepsin, Renin, and several plant proteases such as Papain and Bromelin. The full range and variety of this category, however, includes amylases, proteases, cellulases, as well as other types of enzymes.

Chemical Class 8, Substituted and Derivatized Sulfones:

Sulfones constitute a category of synthetic antibacterial agents, each of which contains the sulfonyl group "R—$SO_2$—R". The members of this chemical class are generally effective against many Gram negative and Gram positive bacteria; and typically function by the same mechanism of action as the sulfonamides. Sulfones however have limited clinical application because of their toxicity.

For this reason, only substituted or derivatized sulfones are used as essential substances in the present invention; and dimethyl sulfone (DMSO) and methylsulfonylmethane (MSM) are the best representatives of this chemical category.

VI. The Collection of Non-Essential Ingredients

A wide collection and selection of non-essential and optionally present compounds and compositions are available as noncompulsory additions and inclusions to the fully formulated dental product. In each instance, however, these optionally present materials are voluntary choice additions to the dental formulations; and will appear and exist as non-requisite and freely elective choice additions to the minimal dental formulations suitable for the making of a commercially salable product. It is must always be remembered however, that these non-essential compounds and compositions are, individually and collectively, always non-mandatory and noncompulsory; and may be freely employed at will or avoided completely and entirely.

Optional Group A, Peroxides:

Peroxides by definition are any compound containing the functional group "—O—O-". Organic peroxides such as lauroyl peroxide are highly reactive oxidizing agents and are used industrially as beaching agents and polymerization catalysts. These organic peroxides are strong irritants and are capable of producing burns and damage to mucous membranes. For these reasons, organic peroxides should be generally avoided in the dental formulations; and if used, should be employed in highly diluted concentrations.

The range of choices intended and expected to be used with the present invention are thus the inorganic peroxides including but not limited to hydrogen peroxide and mineral peroxides, a class exemplified by hydrogen peroxide or HOOH. As long recognized, hydrogen peroxide is a colorless liquid that is soluble in water and ethanol; and is an oxidizing agent which can be used in both concentrated and dilute solutions. Thus, 30% aqueous hydrogen peroxide solutions are used industrially and in laboratory applications as a disinfectant or bleach, while a 3% aqueous solution is conventionally used as a topical anti-infective. In addition, various stabilizers are frequently added to hydrogen peroxide solutions to inhibit its spontaneous decomposition to water [$H_2O$] and molecular oxygen [$O_2$].

In addition, both mineral peroxides and peracids could optionally be incorporated in appropriate amounts.

Optional Group B, Vitamins:

Vitamins by definition and terminology identify a general grouping including a number of unrelated organic substances that occur in many foods (in small amounts) and are necessary for the normal metabolic functioning of the human body. These compositions and compounds may be either water-soluble or fat-soluble; and include all of the following: vitamin A (retinol); vitamin $B_1$ (thiamine); vitamin $B_2$ (riboflavin); vitamin $B_3$ (niacin); vitamin $B_6$ (including pyridoxine, pyridoxal, and pyridoxamine); vitamin $B_7$ (biotin); vitamin $B_{12}$ (cyanocobalamin); vitamin C (acorbic acid); vitamin D (related fat-soluble steroids that have the biological activity of ergocalciferol); vitamin E ($\alpha$-tocopherol); and vitamin K (related fat-soluble compounds all derived from 2-methyl-1, 4-naphthoquinone).

Optional Group C. Nicotinic Acid Salts and Nicotinamide

The nicotinic acid salts of calcium, sodium, magnesium and potassium may be freely added as optional additives to the dental formulations. The nutritional value and benefit of nicotinic acid salts is that they promote local-tissue blood circulation. Derivatives of nicotinic acid may also be optionally added to the formulation at will. Among these derivatives is nicotinamide, which is chemically also known as niacinamide; and is the amide form of niacin [vitamin $B_3$]. Nicotinamide is a constituent of the two coenzymes nicotinamide adenine dinucleotide (NAD) and nicotine adenine dinucleotide phosphate (NADP)—both of which are vital for normal human metabolism.

Optional Group D, Minerals Including Mineral Oxides and Polyoxides, Electrolytes, and Metals:

Minerals by broad general definition are used for nutrition; are considered to be necessary in limited quantities in the human diet; and as such are intended to be consumed daily in at least the minimal recommended doses set forth in the medical and scientific literature. The conventionally recognized common minerals including mineral oxides and polyoxides, to be consumed daily often employ compositions otherwise also known as vitamins (see above), electrolytes, and trace elements; and even a modest listing includes at least the following: ascorbate, folate, nicotinate, riboflavin, thiamine, pyridoxine, cobalamin, calcium, phosphate, iodine, iron, magnesium, and zinc. Other minerals which are typically necessary in very small amounts for health and metabolism are: electrolytes such as sodium, chloride, potassium; trace elements or prosthetic minerals such fluorine, copper, manganese, cobalt, molybdenum, selenium and chromium; and extremely low concentrations of metals such as nickel, silicon, vanadium, and tin.

Other Optional Group Choices:

The other possible substances comprising useful and suitable optional additives is truly enormous. Merely representative and exemplary of these noncompulsory additives are the following:

(i) Ethylene diamine tetraacetic acid or "EDTA", a strong chelating agent for binding magnesium and calcium ions.

(ii) Laminaran, a polysaccharide found in brown seaweed and composed primarily of linked glucose residues.

(iii) Aloe, cinnamon, clove and garlic as naturally occurring antimicrobial agents.

VII. Making the Prepared In-Advance Dental Formulation

The particulars of the dental formulations will be decided and will vary with the chosen ingredients. This pertains to the question of whether or not a carrier is needed; as well as to the choice of which carrier to use for the formulated product. For example, the chosen single essential ingredient or multiple essential and non-essential ingredients for the prepared in-advance product can be admixed in a pre-selected concentration range in an orally acceptable carrier or blending agent such as water, glycerol, alcohol, propylene glycol, fatty alcohols, triglycerides, fatty acid esters, or mineral oils. Other appropriate and suitable carriers and blending agents are represented by liquid petrolatum and the like. In addition, a wide range of viscosity stabilizers and/or pH stabilizers (such as phosphoric acid) and the like may be added if and when necessary.

In addition, the prepared in-advance formulations can be manufactured in multiple or single dose formats; and dispersed in a variety of packaging formats to meet the needs or convenience of the intended consumer.

VIII. Empirically Evaluating the Prepared In-Advance Dental Formulations

To demonstrate the merits and value of the present invention, a series of planned experiments and empirical data are presented below. It will be expressly understood, however, that the experiments described herein and the results provided below are merely the best evidence of the subject matter as a whole which is the present invention; and that the empirical data, while limited in content, is only illustrative of the scope of the present invention as envisioned and claimed.

The illustrative and representative examples of the merits and capabilities of the present invention is also presented below as part of the experimental method. It will be expressly understood, however, that the recited steps and manipulations presented below are merely procedural details, all of which are deemed to be routine and conventional in this field.

Experiment 1

Initially, an accelerated staining test was performed using a very strong coffee concentrate with short periods of immersion. This protocol emulates the actual oral staining process; i.e., live teeth aren't generally submerged in coffee for long periods of time since coffee is only held in the mouth for short periods of time, and the residues are rapidly diluted by saliva. In addition, coffee chemistry and pH changes rapidly due to temperature-excited oxidation—which results in significant acid formation in the first 20 minutes after brewing. As a result, coffee immersion in-vitro for times exceeding 20 minutes exposes test-items to a chemical environment which is not representative of that found in a mouth during a typical human consumption of coffee. While staining occurs over time and with repetition, short immersions in very concentrated coffee provide a staining environment comparable in pH and chemistry to the mouth during sipping.

As one representative example of multiple tests using CHITOSAN NICOTINATE as an essential substance to prevent staining of hydroxyapatite (as found in tooth enamel), 0.02 grams of CHITOSAN NICOTINATE was placed in one of two containers of coffee brewed with 11.0 grams of coffee grounds to 0.5 cups water. Then disks made of hydroxyapatite were immersed in each container for 7 minutes time; and subsequently compared to establish the degree of staining. For meaningful comparisons of staining, the non-CHITOSAN NICOTINATE coffee was used as the dark stain standard, with an arbitrary value of 5. The results showed that for the hydroxyapatite discs immersed in the coffee with CHITOSAN NICOTINATE, the staining was only 1, on a uniform comparison scale where 0 is an un-stained disk.

Experiment 2

As another representative example, multiple tests using high-maltodextrin corn syrup solids/polyglucose were used to prevent staining of hydroxyapatite, as representative of tooth enamel. In this series of tests, 1.5 grams of the high-maltodextrin corn syrup solids/polyglucose was placed in one of two containers of coffee, each of which was then brewed with 11 grams of coffee grounds to 0.5 cups water. Hydroxyapatite disks were then immersed in each container for 7 minutes time; and the subsequently compared to determine the degree of staining. For meaningful comparisons of staining, the non-modified coffee was used as the dark stain standard, with an arbitrary value of 5. The results showed that with high-maltodextrin corn syrup solids/polyglucose the staining of the hydroxyapatite disks was only 3, on a uniform comparison scale where 0 is an un-stained disk.

Experiment 3

As an additional example of multiple tests, POLYETHYLENE GLYCOL was used as the essential substance to prevent staining of hydroxyapatite. In this series of tests, 1 gram of POLYETHYLENE GLYCOL was placed in one of two containers of coffee; and each container of coffee was then brewed with 11 grams of coffee grounds to 0.5 cups water. A plurality of hydroxyapatite disks were then immersed in each container for 7 minutes; and then the disks were compared to determine their degree of staining. For meaningful comparisons of staining, the non-POLYETHYLENE GLYCOL coffee was used as the dark stain standard, with an arbitrary value of 5. The results showed that with POLYETHYLENE GLYCOL, the staining of the hydroxyapatite disks was only 3, on a uniform comparison scale where 0 is an un-stained disk.

In addition, when a previously-coffee-stained hydroxyapatite disk was half-immersed within the brewed coffee for 15 minutes, the coffee-immersed area was lightened by 10%, where the original stain is said to be 100% and an un-stained disk is said to be 0%.

Experiment 4

As a further example of multiple tests, METHYLSULFONYLMETHANE (DIMETHYLSULFONE) was used as an essential ingredient to prevent staining of hydroxyapatite. For this series of tests, 1 gram METHYLSULFONYLMETHANE (DIMETHYLSULFONE) was placed in one of two containers of coffee, each of which was then brewed with 11 grams of coffee grounds to 0.5 cups water. Multiple hydroxyapatite disks were immersed in each container for 7 minutes; and then compared to determine their degree of staining. For meaningful comparisons of staining, the non-METHYLSULFONYLMETHANE (DIMETHYLSULFONE) coffee was used as the dark stain standard, with an arbitrary value of 5. The results showed that for the brew containing METHYLSULFONYLMETHANE (DIMETHYLSULFONE) the staining was only 2, on a uniform comparison scale where 0 is an un-stained disk.

Experiment 5

As one example of multiple tests using protein-splitting enzymes as an essential ingredient to reverse staining of hydroxyapatite, 20 mg of Papain was placed in one container of coffee, which was then brewed with 11 grams of coffee grounds to 0.5 cups water. For this series of tests, only coffee-stained hydroxyapatite disks were then immersed in the freshly brewed coffee for 15 minutes time. The results showed the immersed coffee-stained area was lightened by 20%, based upon a scale where the original stain is deemed to be 100% and an un-stained disk is deemed to be 0%.

Experiment 6

As a representative example of multiple tests using CARDAMOM OIL as the essential ingredient to prevent staining of hydroxyapatite, 6 drops CARDAMOM OIL food flavoring was placed in one of two containers of coffee each of which was brewed with 11 grams of coffee grounds to 0.5 cups water. A plurality of hydroxyapatite disks are then immersed in each container for 7 minutes time; and the immersed disks compared to determine their degree of staining. For meaningful comparisons of staining, the non-CARDAMOM OIL coffee was used as the dark stain standard, with an arbitrary value of 5. The empirical results showed that with CARDAMOM OIL, the staining was only 4, on a uniform comparison scale where 0 is an un-stained disk.

Experiment 7

As one representative example of multiple tests using a combination of some of essential ingredients to prevent wine staining of tooth enamel, a hydroxyapatite disk was immersed in 0.5 cups wine to which was added PEG 8000 (0.875 gm), Starch Carbohydrate MD 42 (1.0 gm), MSM (0.625 gm), and a solution of Chitosan Nicotinate (0.29 gm solution for 0.013 grams Chitosan). The results showed that 2 hours of hydroxyapatite immersion produced no discernible color change.

Experiment 8

We built a flow cell system to stain extracted teeth and hydroxyapatite (HAP) disks. A combination of coffee, human saliva, and artificial saliva products at a pH of 6.8 and was mixed, and circulated through the flow system in contact with the HAP disks at a velocity of 40 cm per minute for about 2 hours with a base temperature of 37° C. (98.6 F) and intermittent 30-second thermal spikes to 82° C. (180° F.) to emulate the actual process of tooth-staining from coffee consumption. The resulting stained HAP disks were rinsed in artificial saliva dried for about 2 hours at room temperature. Once the HAP disks were dry, each disk's coloration was photo-documented for comparison to the post-product-immersion staining of that disk.

In order to assess the stain reversal capacity of the product, product was mixed with coffee and run through the flow cell: to 125 ml of coffee, or 0.5 cups, to perform an accelerated verification of the stain-reversal capabilities of the product (since this is 2 times the concentration recommended to be consumed). This coffee-product solution was circulated over stained disks at a velocity of 40 cm per minute for about 10 minutes, then replaced with fresh solution, each time with a base temperature of 37° C. (98.6 F) and intermittent 30-second thermal spikes to 82° C. (180° F.) to emulate the actual process of coffee consumption.

With a percent-scale where an unstained disk is 0% and the stained disk is 100%, visual analysis showed and average stain reduction of well over 70% for this test series.

Experiment 9

As an additional example of testing of the synergy of the preferred ingredients in reversing existing staining, extracted teeth and hydroxyapatite disks were stained both in beakers and in a flow-cell system, using a staining solution consisting of either natural or artificial saliva and concentrated coffee.

The prepared teeth and disks were then evaluated via instrumented and/or photographic evaluation of initial staining, exposed to various combinations of the listed ingredients in coffee, and again evaluated via instrumentation and/or photography for subsequent stain reversal.

As an example of testing accomplished with the preferred complement of ingredients, mixed with coffee this combination of ingredients was added to 125 ml of coffee, or 0.5 cups, to perform an accelerated verification of the stain-reversal capabilities of the product (since this is 2 times the concentration recommended to be consumed). Stained HAP disks, as referenced above, were photo-documented and then immersed in the above solution for 5 minutes, removed from the solution, and re-immersed in a fresh mixture of the same solution. This resulted in more than 50% reduction in staining area, and approximately 80% reduction of the darkest stains.

The present invention is not to be restricted in form, nor to be limited in scope, except by the claims appended hereto.

What is claimed is:

1. A composition for enhancing an appearance and quality of teeth in a living subject, said composition comprising in combination:
   a foodstuff containing a tooth staining agent as a constituent thereof of coffee; and
   a non-toxic, biocompatible, and orally acceptable dental formulation comprising:
      a cellulose-like biopolymer, at least one of a glycol and a polygylcol, at least one of a starch and a dextrin, and a sulfone.

2. A composition for enhancing an appearance and quality of teeth in a living subject, said composition comprising in combination:
   a foodstuff containing a tooth staining agent as a constituent thereof of tea; and
   a non-toxic, biocompatible, and orally acceptable dental formulation comprising:
      a cellulose-like biopolymer consisting of around 0.02 grams, at least one of a glycol and a polygylcol consisting of around 1.0 gram, at least one of a starch and a dextrin consisting of around 1.5 grams, and a sulfone consisting of around 1.0 gram.

3. The composition of claim 2 wherein said dental formulation further includes at least one substance selected from a group consisting of waxes, and protein-splitting enzymes.

4. The composition of claim 1 or 2 wherein said dental formulation further includes at least one additive selected from the group consisting of peroxides, nicotinic acid salts and nicotinamide, mineral oxides and polyoxides.

5. The composition of claim 1 or 2 wherein said dental formulation is water soluble.

6. The composition of claim 1 or 2 wherein said dental formulation is water miscible.

7. The composition of claim 1 or 2 wherein said dental formulation is a powder.

8. The composition of claim 1 or 2 wherein said dental formulation is a liquid.

9. The composition of claim 1 or 2 wherein said dental formulation interacts with the staining agents in said foodstuff by changing a pigmentation of said agents.

10. The composition of claim 1 or 2 wherein said dental formulation interacts with the staining agents in said foodstuff by preemptively occupying binding sites of said agents.

11. The composition of claim 1 or 2 wherein said dental formulation interacts with said staining agents.

* * * * *